(12) United States Patent
Bluth et al.

(10) Patent No.: US 8,187,810 B2
(45) Date of Patent: May 29, 2012

(54) METHOD FOR DIAGNOSING OVERACTIVE BLADDER

(75) Inventors: Martin Heath Bluth, West Hempstead, NY (US); Wellman W. Cheung, Briarwood, NY (US)

(73) Assignees: Wellman Wai-Man Cheung, Briarwood, NY (US); Martin Heath Bluth, Southfield, MI (US)

( * ) Notice: Subject to any disclaimer, the term of this patent is extended or adjusted under 35 U.S.C. 154(b) by 707 days.

(21) Appl. No.: 12/116,307

(22) Filed: May 7, 2008

(65) Prior Publication Data
US 2008/0286790 A1 Nov. 20, 2008

Related U.S. Application Data

(60) Provisional application No. 60/938,299, filed on May 16, 2007.

(51) Int. Cl.
*C12Q 1/68* (2006.01)
(52) U.S. Cl. ........................................ 435/6.11; 435/6.1
(58) Field of Classification Search ........................ None
See application file for complete search history.

(56) References Cited

U.S. PATENT DOCUMENTS

2001/0051344 A1* 12/2001 Shalon et al. ...................... 435/6
2003/0148394 A1* 8/2003 Silos-Santiago et al. ....... 435/7.2

FOREIGN PATENT DOCUMENTS

WO WO 2004112589 A2 * 12/2004
WO WO 2005042725 A2 * 5/2005

OTHER PUBLICATIONS

Jivotovskaya et al. Eukaryotic trnaslation initiation factor 3 (eIF3) and eIF2 can promote mRNA binding to 40S subunits independently of eIF4G in yeast. Molecular and Cellular Biology, vol. 26, No. 4, pp. 1355-1372, Feb. 2006.*

Krushkal et al. Evolutionary relationships among proteins encoded by the regulator of compement activation gene cluster. Molecular Biology and Evolution, vol. 17, No. 11, pp. 1718-1730, 2000.*

Wiesen et al. Identification and characterization of layer-specific differences in extraocular muscle M-bands. Investigative Ophthalmology & Visual Science, vol. 48, No. 3, Mar. 2007.*

Sorensen et al. Blood cell gene expression profiling in subjects with aggressive periodontitis and chronic arthritis. Journal of Periodontology, vol. 79, No. 3, pp. 477-485, Mar. 2008, Abstract only.*

Hoch et al. Roles of PDGF in animal development. Development, vol. 130, pp. 4769-4784, 2003.*

Faraco et al. Characterization of the human gene for microfibril-associated glycoprotein (MFAP2), assignement to chromosome 1p36.1-p35, and linkage to D1S170. Genomics, vol. 25, pp. 630-637, 1995.*

GenBank Accession No. NM_001009554.1, GI: 57222337, Nov. 2006.*

GenBank Accession No. NM_021647.5, GI: 57222248, Nov. 2006.*

Tajsharghi et al. Distal arthrogryposis and muscle weakness associated with a beta-tropomyosin mutation. Neurology, vol. 68, No. 10, pp. 772-775, Mar. 2007.*

Gardina et al. Alternative splicing and differential gene expression in colon cancer detected by a whole genome exon array. BMC Genomics, vol. 7, p. 325, Dec. 2006.*

Pusztai and Hess. Clinical trial design for microarray predictive marker discovery and assessment. Annals of Oncology, vol. 15, pp. 1731-1737, 2004.*

Golub et al. Molecular classification of cancer: class discovery and class prediction by gene expression monitoring. Science, vol. 286, pp. 531-537, Oct. 1999.*

Bluth, Bluth, Johns, Khan, Lin, Zenilman and Cheung. Peripheral blood mononuclear cell gene expression array profiles in patients with overactive bladder. The Journal of Immunology, vol. 178, abstract 132.8, Apr. 1, 2007.*

* cited by examiner

*Primary Examiner* — Jennifer Dunston
(74) *Attorney, Agent, or Firm* — Senniger Powers LLP

(57) ABSTRACT

Techniques for diagnosing overactive bladder (OAB) in a patient are provided. For example, a technique for diagnosing overactive bladder in a patient includes the step of obtaining peripheral blood mononuclear cells (PBMC) from the patient to provide a reporter function in the patient.

4 Claims, 1 Drawing Sheet

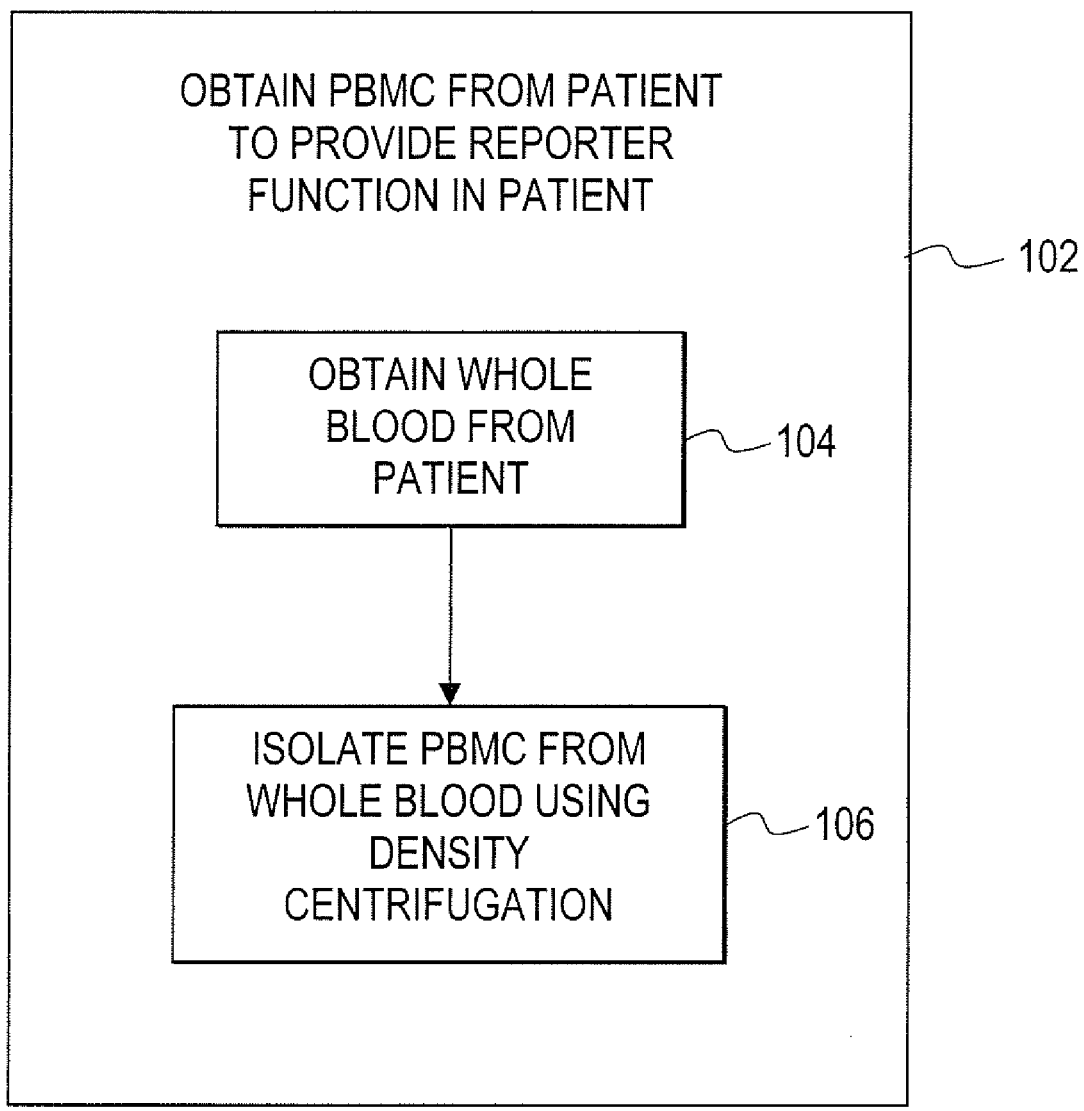

METHOD FOR DIAGNOSING OVERACTIVE BLADDER

CROSS-REFERENCE TO RELATED APPLICATION(S)

This application claims the benefit of U.S. Provisional Application Ser. No. 60/938,299, filed on May 16, 2007, the disclosure of which is incorporated by reference herein.

FIELD OF THE INVENTION

The present invention relates generally to immunology and, more particularly, to diagnosing overactive bladder.

BACKGROUND OF THE INVENTION

Overactive bladder (OAB) is a highly prevalent urological disorder affecting both men and women. OAB is treatable, but many afflicted patients remain undiagnosed or untreated, due, in large part, to the invasive existing diagnostic approaches. Furthermore, OAB can be presented in patients with or without bladder outlet obstruction (such as benign prostatic hypertrophy) or bladder neck dysfunction. Very often, making the correct diagnosis in these patients can be very difficult.

OAB continues to present diagnostic challenges, and confirmation of disease often requires invasive procedures. For example, OAB is generally diagnosed by history and/or confirmed by invasive technology called urodynamic testing or urodynamics. Essentially any procedure designed to provide information about a bladder problem can be called a urodynamic test. The type of test utilized depends on the problem to be diagnosed.

Most urodynamic testing focuses on the bladder's ability to empty steadily and completely. It can also show whether the bladder is having abnormal contractions that cause leakage. Urodynamic tests can range from simple observation to precise measurement using sophisticated instruments. Thus, urodynamic testing can provide useful information regarding bladder function. Unfortunately, however, urodynamic testing is also a highly invasive procedure which typically involves inserting a catheter into the bladder, giving the patient known amounts of fluid, and checking bladder capacity, involuntary voiding, and muscular control as objective findings.

Similarly, urinary incontinence is a urological disorder that can include, for example, stress-type incontinence (that is, leakage of urine with coughing, sneezing, etc.), urge-type incontinence (that is, leakage of urine associated with a strong sensation to void), mixed-type incontinence (that is, a combination of stress-type and urge-type incontinence) and overflow incontinence (that is, when patients cannot urinate it will overflow and lead to incontinence).

Patients with urgency or urge-type incontinence represent a group of overactive bladder sufferers whose diagnosis remains difficult to establish. Urodynamic testing demonstrating involuntary bladder contraction provides objective confirmation but represents an invasive approach and is therefore undesirable.

Accordingly, there exists a need for techniques to diagnose and monitor response to treatment of urological disease that obviate the need for existing invasive procedures.

SUMMARY OF THE INVENTION

The present invention, in illustrative embodiments thereof, provides techniques for diagnosing overactive bladder (OAB).

In accordance with one aspect of the invention, a technique for diagnosing a urological disease in a patient includes the step of obtaining peripheral blood mononuclear cells (PBMC) from the patient to provide a reporter function in the patient.

These and other features, aspects and advantages of the present invention will become apparent from the following detailed description of illustrative embodiments thereof, which is to be read in connection with the accompanying drawing(s).

BRIEF DESCRIPTION OF THE DRAWING(S)

FIG. 1 is an exemplary method for diagnosing OAB in a patient, in accordance with an illustrative embodiment of the present invention.

DETAILED DESCRIPTION OF THE INVENTION

OAB, as noted above, presents diagnostic difficulties and confirmation of disease often requires invasive approaches. A blood-based assay with appropriate diagnostic sensitivity and specificity would obviate these invasive testing procedures.

It has been demonstrated that peripheral blood mononuclear cells (PBMC) can provide a reporter function in solid organ retroperitoneal disease. As described herein, we investigate, for example, the utility of using PBMC as a marker for patients with OAB and the utility of using PBMC as a marker for patients with confirmed involuntary bladder contraction. The term "patient" as used herein is intended to refer broadly to mammalian subjects, and more preferably refers to humans receiving medical attention (e.g., diagnosis, monitoring, etc.), care or treatment.

By way of example, one or more embodiments of the invention can be prepared and/or conducted in a manner as described below.

Twenty-one patients were assessed (as demonstrated by urodynamics) for OAB and structural integrity (for example, pelvic prolapse, bladder neck dysfunction, bladder capacity, stress incontinence, and involuntary bladder contraction). Patients with a history of recent surgery, infection, or positive valsalva leak point pressure or negative for involuntary bladder contraction, as demonstrated by urodynamics, were excluded. Whole blood was obtained from patients and appropriately matched controls (n=6) and peripheral blood mononuclear cells (PBMC) were separated by density centrifugation (Ficoll-Paque™, a registered trademark of GE Healthcare Bio-Sciences AB, LLC).

Ribonucleic acid (RNA) was isolated from PBMC and converted to complementary (cRNA) and subjected to microarray analysis (human U133A 2.0 gene chip). Data are expressed as fold change and were analyzed using Lima Package from Bioconductor. Genes with greater than 2-fold change were considered positive.

Changes between patients with OAB were compared with healthy controls as a total, and we also separated these comparisons into OAB versus controls for men only and women only. The analysis can have gender-based importance as some genes which are hormonally-linked behaved differently in each gender. For example, PGRMC1 (progesterone receptor membrane component 1) was found to be downregulated in females with OAB but not in males, suggesting that sex-based analysis can provide additional genes of interest which can serve to diagnose or monitor treatment response to OAB in females as compared to males.

In connection with the preparatory techniques described above, one or more embodiments of the invention are described below. The average patient age was 51 (range =31-73) and were predominantly female (76%). The majority of patients had involuntary bladder contraction (62%), and stress incontinence (52%), and most female patients had pelvic prolapse (69%). Forty-three percent of patients had bladder neck dysfunction and all patients had normal to low bladder capacity. Microarray analysis revealed that 16 genes were differentially regulated (8 upregulated and 8 downregulated) in all patients with OAB compared with controls. By way of example, PGRMC1 (progesterone receptor membrane component 1), EIF2S3 (eukaryotic initiation factor), C3AR1 (complement receptor) and 3 unknown genes were downregulated. Upregulated genes included, for example, MYOM2 (myomesin M-protein), a cytoskeletal protein involved in structural integrity.

Gender-based analysis demonstrated 74 genes differentially regulated in males (25 upregulated and 49 downregulated), and 30 in females (13 upregulated and 17 downregulated). Of these, platelet-derived growth factor (PDGF), MFAP3L (a microfibrillar-associated protein), and TPM1 (tropomyosin) were downregulated in all sets analyzed. PDGF, MFAP3L and TPM1, as is well-known in the art, have structurally-related importance as a result of similarity to structural function.

Microarray analysis revealed many genes which were differentially regulated in PBMC from OAB patients. For example, OAB patients, including those with involuntary detrusor contractions, exhibited differential expression of regulatory/structural genes when compared with healthy controls. To this end, PDGF, MFAP and TPM1, as illustrated herein, may be important in regulating structural integrity of bladder and supporting tissues. These data suggest that PBMC provides a reporter function for patients with OAB (for example, involuntary bladder contractions).

As described herein, one or more embodiments of the present invention include a non-invasive, safe method of providing biomarkers (that is, substances used as indicators of one or more biologic states) for disease when compared with biopsy of solid organ. A biomarker can be a substance whose detection indicates a particular disease state. More specifically, a biomarker indicates a change in expression or state of a protein that correlates with the risk or progression of a disease, or with the susceptibility of the disease to a given treatment.

With reference to FIG. 1, an exemplary method 100 is shown for diagnosing OAB in a patient, in accordance with an illustrative embodiment of the present invention. In step 102 of method 100, PBMC is obtained from the patient to provide a reporter function in the patient. Obtaining PBMC from a patient may include obtaining whole blood from a patient (step 104), for example in an amount in a range of about four to six milliliters (ml), and isolating PBMC from the whole blood (step 106), for example using density centrifugation. Providing a reporter function in the patient may include processing the PBMC to isolate RNA for analysis. Such analysis includes comparing gene changes in the patient versus gene changes in a control sample to provide a screening modality to ascertain one or more genes involved in a pathogenesis of OAB.

Providing a reporter function in the patient may include, for example, processing the PBMC to isolate RNA for analysis, wherein the analysis may include comparing gene changes in the patient versus gene changes in a control sample to provide a screening modality to ascertain one or more genes involved in the pathogenesis of OAB.

As noted above, comparing gene changes in a patient versus gene changes in a control samples provides a screening modality to mine for unique genes potentially involved in the pathogenesis of OAB.

Although illustrative embodiments of the present invention have been described herein, it is to be understood that the invention is not limited to those precise embodiments, and that various other changes and modifications may be made by one skilled in the art without departing from the scope or spirit of the invention.

What is claimed is:

1. A method of diagnosing overactive bladder (OAB) in a human patient, the method comprising:
   isolating ribonucleic acid (RNA) from peripheral blood mononuclear cells (PBMC) of the patient and from the PBMC of at least one appropriately matched control subject;
   converting the RNA to complementary RNA (cRNA); and
   subjecting the cRNA to microarray analysis to determine cRNA levels of at least one gene selected from the group consisting of platelet-derived growth factor (PDGF), microfibrillar-associated protein 3-like (MFAP3L), and tropomyosin 1 (TPM1), wherein a difference in the cRNA levels of said at least one gene between the patient's cRNA and the cRNA of the at least one appropriately matched control subject indicates that the patient be diagnosed with OAB.

2. The method of claim 1, further comprising, prior to the isolating step, the steps of obtaining whole blood from the patient in an amount in a range of about four to six milliliters (ml); and
   isolating PBMC from the whole blood by density centrifugation.

3. A method of diagnosing overactive bladder (OAB) in a female human patient, the method comprising:
   isolating ribonucleic acid (RNA) from peripheral blood mononuclear cells (PBMC) of the female patient and from the PBMC of at least one appropriately matched female control subject;
   converting the RNA to complementary RNA (cRNA); and
   subjecting the cRNA to microarray analysis to determine cRNA levels of at least one gene selected from the group consisting of progesterone receptor membrane component 1 (PGRMC1), eukaryotic translation initiation factor 2 subunit 3 (EIF2S3), complement component 3a receptor 1 (C3ARI), and myomesin M-protein 2 (MYOM2),
   wherein a difference in the cRNA levels of said at least one gene between the female patient's cRNA and the cRNA of the at least one appropriately matched female control subject indicates that the female patient be diagnosed with OAB.

4. The method of claim 1, further comprising, prior to the isolating step, the steps of obtaining whole blood from the patient in an amount in a range of about four to six milliliters (ml); and
   isolating PBMC from the whole blood by density centrifugation.

* * * * *